United States Patent
Ciceri et al.

(10) Patent No.: US 10,905,657 B2
(45) Date of Patent: Feb. 2, 2021

(54) SOLID DISPERSIONS OF COENZYME $Q_{10}$

(71) Applicant: Indena S.P.A., Milan (IT)

(72) Inventors: Daniele Ciceri, Milan (IT); Federico Peterlongo, Milan (IT); Massimo Ronchi, Milan (IT)

(73) Assignee: Indena S.P.A., Milan (IT)

( * ) Notice: Subject to any disclaimer, the term of this patent is extended or adjusted under 35 U.S.C. 154(b) by 0 days.

(21) Appl. No.: 15/579,975

(22) PCT Filed: Jun. 10, 2016

(86) PCT No.: PCT/EP2016/063262
§ 371 (c)(1),
(2) Date: Dec. 6, 2017

(87) PCT Pub. No.: WO2016/198576
PCT Pub. Date: Dec. 15, 2016

(65) Prior Publication Data
US 2018/0200201 A1 Jul. 19, 2018

(30) Foreign Application Priority Data
Jun. 12, 2015 (EP) .................. 15171943

(51) Int. Cl.
*A61K 31/12* (2006.01)
*A61K 31/122* (2006.01)
*A61K 9/14* (2006.01)

(52) U.S. Cl.
CPC ........... *A61K 31/122* (2013.01); *A61K 9/145* (2013.01); *A61K 9/146* (2013.01)

(58) Field of Classification Search
CPC ....................... A61K 31/122; A61K 9/146
See application file for complete search history.

(56) References Cited

U.S. PATENT DOCUMENTS

2011/0142914 A1* 6/2011 Persaud ............ A61K 9/0075
424/450

FOREIGN PATENT DOCUMENTS

| CN | 101272769 A | 9/2008 |
|---|---|---|
| CN | 103536574 A | 1/2014 |
| DE | 4327063 A1 | 2/1995 |
| EP | 2087887 A1 | 8/2009 |
| JP | 2000507594 A | 6/2000 |
| WO | 2007086689 A1 | 8/2007 |
| WO | 2012129072 A1 | 9/2012 |

OTHER PUBLICATIONS

International Preliminary Report on Patentability of PCT/EP2016/063262 dated Aug. 21, 2017.
Search Report and Written Opinion of PCT/EP2016/063262 dated Aug. 10, 2016.
Chinese Office Action dated Mar. 25, 2020 in connection with corresponding Chinese Application Serial No. 201680032963.7.
English translation of Office Action dated May 18, 2020 in connection to corresponding Japanese Application No. 2017-563338.
Letter reporting office action of Japanese Patent Application No. 2017-563338 dated Jun. 17, 2020.

* cited by examiner

*Primary Examiner* — Shobha Kantamneni
(74) *Attorney, Agent, or Firm* — Silvia Salvadori, P.C.; Silvia Salvadori

(57) ABSTRACT

The invention relates to a solid dispersion comprising Coenzyme $Q_{10}$ and a phospholipid, in the presence of a cellulosic derivative and/or a polymeric material selected from the group consisting of polyvinylpyrrolidone, polyvinyl acetate, poly (methacrylic acid, methyl methacrylate), poloxamers, chitosan, alginates, hyaluronic acid, pectin, pullulan, cyclodextrins, starch polymers, D-alpha-tocopheryl polyethylene glycol 1000 succinate.

9 Claims, No Drawings

SOLID DISPERSIONS OF COENZYME $Q_{10}$

This application is a U.S. national stage of PCT/EP2016/063262 filed on 10 Jun. 2016, which claims priority to and the benefit of European Application No. 15171943.2 filed on 12 Jun. 2015, the contents of which are incorporated herein by reference in their entireties.

The present invention relates to solid dispersions comprising Coenzyme $Q_{10}$ and phospholipids, to a process for their preparation and to pharmaceutical, nutraceutical and cosmetic compositions containing them.

Coenzyme $Q_{10}$, also known as ubidecarenone or ubiquinone, is a lipophilic endogenous substance present in most eukaryotic cells, primarily concentrated in mitochondria. Coenzyme $Q_{10}$ participates to the mitochondrial oxido-reductive reactions of electron transport chain for the generation of energy, in the form of Adenosine Triphosphate (ATP). Coenzyme $Q_{10}$ can exist in three oxidation states: (1) the fully reduced form (ubiquinol), (2) the radical intermediate form (semiquinone), and (3) the fully oxidized form (ubiquinone). Coenzyme $Q_{10}$ exists in our body in all these forms and a physiological equilibrium between the oxidized and the reduced form is maintained.

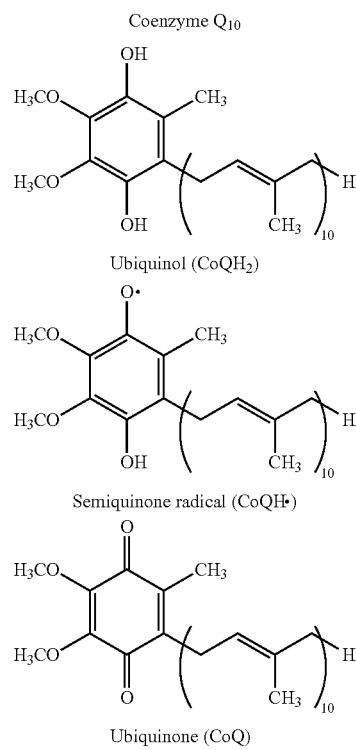

The name ubidecarenone or ubiquinone (or ubiquinol for the reduced form) is related to the fact that Coenzyme $Q_{10}$ is ubiquitously distributed in the organs of the human body, but it is primarily concentrated in organs with a higher energy requirement, like heart, liver and kidney.

The name ubiquinone also refers to its quinone structure, while the number 10 is the number of isoprenyl units in its tail.

Coenzyme $Q_{10}$ can also be introduced in human body with the diet, even if the contribution of endogenous Coenzyme $Q_{10}$ to its physiological plasma levels has not been clarified. The richer sources of dietary Coenzyme $Q_{10}$ include meat, poultry and fish, while fruits, vegetables and eggs are limited sources of Coenzyme $Q_{10}$.

As Coenzyme $Q_{10}$ deficiency is a rare, oral coenzyme $Q_{10}$ supplementation is mainly used to maintain homeostasis of the body, to promote heart health, as energy booster and also to treat different diseases like ageing, periodontal disease, impaired memory, fatigue, coronary disease, high blood pressure, immune system impairment.

Coenzyme $Q_{10}$ supplementation can be particularly useful for elderly people, as the tissue and plasma physiological levels of Coenzyme $Q_{10}$ are reported to decline with age.

Coenzyme Q10 is a yellow-orange crystalline powder, with a low melting point (about 50° C.).

The activity of Coenzyme $Q_{10}$ supplementation can be strongly limited by its poor pharmacokinetic properties and, in particular, by its very low oral bioavailability, due to the fact that Coenzyme $Q_{10}$ is commercialized in a totally crystalline form and it is characterized by high lipophilicity and relatively high molecular weight.

Several formulation approaches have been applied to promote $CoQ_{10}$ bioavailability, including self-emulsifying delivery systems, inclusion in cyclodextrins, solid dispersion, lipophilic formulations, microspheres, nanoparticles, etc., but absorption of Coenzyme $Q_{10}$ into the systemic circulation still remains a challenge.

It has now been found that preparing a solid dispersion of Coenzyme $Q_{10}$ and phospholipids, in the presence of other ingredients such as cellulose derivatives (methylcellulose, hydroxypropylcellulose, hydroxypropylmethyl cellulose, microcrystalline cellulose, and the like) and/or other polymeric materials including but not limited to polyvinylpyrrolidone, polyvinyl acetate, poly (methacrylic acid, methyl methacrylate), poloxamers and the like, allows a high degree of amorphization of Coenzyme $Q_{10}$, determining an increased solubility, a faster dissolution rate and hence a better oral bioavailability.

The above mentioned cellulosic derivatives and other polymeric materials can contribute to stabilize the amorphous form of Coenzyme $Q_{10}$ in order to avoid its re-crystallization in the less bioavailable crystalline form.

The role of phospholipids may not be limited to facilitate the dispersion of Coenzyme $Q_{10}$ in the gastro-intestinal fluids, but can also have the effect of enhancing the capacity of Coenzyme $Q_{10}$ to cross the lipid-rich biomembranes and to reach the circulation.

These solid dispersions are also characterized by suitable technological properties to be easily incorporated in different dosage forms to allow an easy administration.

The present invention relates to a solid dispersion comprising:
 a) Coenzyme Q10
 b) a phospholipid,
 c) one or more a cellulosic derivative selected from the group consisting of carboxymethyl cellulose, methylcellulose, ethyl cellulose, hydroxypropylcellulose, hydroxyethyl cellulose, hydroxypropylmethyl cellulose, microcrystalline cellulose, cellulose acetate phthalate, hydroxypropylmethyl cellulose phthalate; and/or
 d) a polymeric material selected from the group consisting of polyvinylpyrrolidone, polyvinyl acetate, poly (methacrylic acid, methyl methacrylate), poloxamers, chitosan, alginates, hyaluronic acid, pectin, pullulan, cyclodextrins, starch polymers, D-alpha-tocopheryl polyethylene glycol 1000 succinate.

The phospholipid may be selected from the group consisting of lecithins from soy, sunflower or egg, phosphatidyl choline, phosphatidyl serine, phosphatidyl ethanolamine, in which the acyl groups may be the same or different are mostly derived from palmitic, stearic, oleic, linoleic, linolenic acids.

In the present invention, all ratios are weight ratios.

The Coenzyme $Q_{10}$/phospholipid ratio is preferably 0.2 to 2, most preferably 0.5 to 1.

The Coenzyme $Q_{10}$ to cellulosic derivative ratio is preferably 0.2 to 2, most preferably 0.5 to 1.

The Coenzyme $Q_{10}$ to polymeric material ratio is 0.2 to 10, most preferably 0.5 to 5.

The solid dispersions of the invention provide Coenzyme $Q_{10}$ with an increased degree of amorphization and a reduced tendency to recrystallize in a less bioavailable form. The solid dispersions have improved the technological properties facilitating the incorporation of the complex in different pharmaceutical, nutraceutical and cosmetic formulations.

The solid dispersions, according to the present invention, are prepared by a method comprising the steps of:

i) preparing a suspension of the one or more cellulosic derivative, the phospholipid and/or the polymeric material in an organic solvent;

ii) preparing a solution of coenzyme Q10 in an organic solvent;

iii) mixing the solution obtained in step ii) with the suspension obtained in step i);

iv) stirring the suspension obtained in step iii) at a temperature between 40° C. and 70° C.;

v) removing the solvent preferably under reduced pressure from the suspension obtained in step iv).

The organic solvent is preferably ethanol, acetone and ethyl acetate, most preferably ethyl acetate.

The obtained powder is then calibrated and eventually grinded to obtain the desired particle size distribution.

The obtained solid dispersions were analyzed for HPLC content of Coenzyme $Q_{10}$, for water content and for residual solvent.

A calorimetric analysis by Differential Scanning calorimetry (DSC) was also performed to calculate, on the basis of the reduction of the enthalpy of fusion (J/g), the degree of amorphization of Coenzyme $Q_{10}$ in the solid dispersion, in comparison with the totally crystalline Coenzyme $Q_{10}$.

It has been found that the phospholipids dispersions disclosed in the present invention are characterized by a high level of amorphization of Coenzyme $Q_{10}$. The amorphization of Coenzyme Q10 combined with the positive effect of phospholipids to enhance the capacity of molecules to cross the lipid-rich biomembranes, can play a synergistic effect providing a higher oral bioavailability.

Another object of the invention are formulations for oral administration containing the solid dispersions of the invention and pharmaceutically and food acceptable materials such as an excipient, disintegrant, lubricant, binder, coating agent, colorant, absorption promoter, solubilizing agent, stabilizer, flavor, sweetener, antiseptic, preservative, antioxidant and the like.

Examples of dosage forms of the formulations of the invention include, without limitation, chewable tablets, capsules, soft gelatin capsules, hard gelatin capsules, caplets, lozenges, chewable lozenges, health bars, confections, animal feeds, cereals, cereal coatings, and combinations thereof. The preparation of the above dosage forms are well known to persons of ordinary skill in the art.

The composition for oral administration of the present invention can be used for a variety of purposes for improving the quality of life (QOL) of humans, including the prevention and treatment for various diseases, reduction of side reactions, promotion of recovery from disease and the like, and can also be used for the purpose of maintaining and promoting daily health and the like. The dosage of the composition for oral administration of the present invention is not subject to limitation, and is preferably 1 to 1200 mg per day for a human, based on the amount of Coenzyme $Q_{10}$, more preferably 10 to 800 mg, and from the viewpoint of routine ingestion and onset of effects, it is particularly preferably 30 to 500 mg. The above-described daily amount can be taken at one time or in several divided portions. Duration of ingestion is not subject to limitation.

The oral bioavailability of the solid dispersion of Coenzyme $Q_{10}$ was evaluated in rats in comparison with Coenzyme $Q_{10}$ administered as crystalline powder. The preliminary results show an improved oral bioavailability of the solid dispersion of Coenzyme $Q_{10}$ with phospholipids in comparison with unformulated Coenzyme $Q_{10}$.

EXAMPLES

Example 1—Preparation of the Solid Dispersion 1.5 Kg of microcrystalline cellulose, 2.0 Kg of sunflower lecithin and 0.5 Kg of cellulose ethers (methyl cellulose and hydroxypropylmethyl cellulose) were suspended in 50 liters of ethyl acetate and refluxed for one hour. The resulting suspension was cooled to 40° C.

1 Kg of Coenzyme $Q_{10}$ was dissolved in 30 liters of ethyl acetate at 20-25° C. in the dark. The obtained solution was filtered and added to the suspension of microcrystalline cellulose, sunflower lecithin and cellulose ethers. The obtained suspension was stirred at 40° C. for about one hour.

The solvent was then removed under reduced pressure until a soft mass was obtained. The latter was dried at 50° C. under vacuum for 16 hours, until a residual of Ethyl acetate lower than 5000 ppm.

The resulting solid was calibrated through a 2 mm screen to obtain a yellow-orange solid Example 2—Characterization of the Solid Dispersion: Differential Scanning Calorimetry The solid dispersion of Coenzyme Q10 with phospholipid was analyzed by Differential Scanning calorimetry (DSC) in comparison with crystalline Coenzyme $Q_{10}$.

The analyses were performed using a Mettler DSC1 System. Heat flow was recorded from 30 to 300° C. with linear heating rate (10° C./min), using closed aluminium crucibles (40 µl volume) with a pinhole, under a 50 ml/min nitrogen flow.

About 5-10 mg of powder were used for each measurement. The thermal profiles were acquired and elaborated by a dedicated software.

The degree of amorphization of Coenzyme $Q_{10}$ in the solid dispersion was in the range 30-40% and it was calculated on the basis of the reduction of the enthalpy of fusion.

Example 3—Pharmacokinetic Study in Rats

Pharmacokinetic parameters ($T_{max}$, $C_{max}$, absolute bioavailability) were determined in rats after the oral administration of a single dose of Coenzyme $Q_{10}$ as crystalline powder and as solid dispersion with phospholipids.

Male Sprague-Dawley rats, weighting 300-350 g were used for the pharmacokinetic experiment. Rats were fasted 16 hours before administration with free access to water.

Coenzyme $Q_{10}$ as crystalline powder and as solid dispersion with phospholipids were suspended in 1% carboxymethyl cellulose water suspension and administered by intragastric gavage as a single dose of 50 mg of Coenzyme $Q_{10}$/Kg.

Blood samples were collected from tail vein after 0.5-1.0-2.0-4.0-8.0-12.0 and 24 hours after administration.

Plasma was obtained from blood samples by centrifugation at 5.000×g for 15 minutes and kept frozen (−20° C.) until analysis. After protein sedimentation, Coenzyme $Q_{10}$ was extracted by plasma samples with n-hexane; the extraction step with hexane was repeated for three times. The hexane phases, separated by centrifugation, were collected and the solvent was removed by evaporation under nitrogen. The residue was dissolved in 2-propanol for HPLC/MS analysis at 275 nm, using internal standard method for Coenzyme $Q_{10}$ quantification.

The following pharmacokinetic parameters were calculated:

| Parameter | Crystalline Coenzyme $Q_{10}$ | Coenzyme $Q_{10}$ solid dispersion with phospholipids |
|---|---|---|
| $T_{max}$ (hours) | 3.8 | 4.0 |
| $C_{max}$ (µg/ml) | 0.23 | 1.35 |
| AUC 0-24 (µg · h/ml) | 4.1 | 29.2 |

Example 4—Formulations Containing the Solid Dispersion of Coenzyme $Q_{10}$ with Phospholipid Film-Coated Tablets

| | |
|---|---|
| Coenzyme $Q_{10}$ solid dispersion | 400.0 mg |
| Microcrystalline cellulose | 200.0 mg |
| Dicalcium phosphate anhydrous | 146.0 mg |
| Sodium croscarmellose | 30.0 mg |
| Silicon dioxide | 8.0 mg |
| Talc | 8.0 mg |
| Magnesium stearate | 8.0 mg |
| Film-coating | 20.0 mg |

Example 5—Formulation Containing the Solid Dispersion of Coenzyme $Q_{10}$ with Phospholipids Soft Gelatin Capsules

| | |
|---|---|
| Coenzyme $Q_{10}$ solid dispersion | 250.0 mg |
| Flaxseed oil | 384.0 mg |
| Glyceryl monostearate | 10.0 mg |
| Lecithin | 6.0 mg |

The invention claimed is:

1. A solid dispersion comprising:
   a) Coenzyme Q10
   b) a phospholipid,
   c) one or more a cellulosic derivative selected from the group consisting of carboxymethyl cellulose, methylcellulose, ethyl cellulose, hydroxypropylcellulose, hydroxyethyl cellulose, hydroxypropylmethyl cellulose, microcrystalline cellulose, cellulose acetate phthalate and hydroxypropylmethyl cellulose phthalate;
   wherein the Coenzyme Q10 to phospholipid ratio is 0.5 to 1, and the phospholipid is the only surfactant,
   said solid dispersion being obtained by a method comprising the steps of:
   i) preparing a suspension of the one or more cellulosic derivative, the phospholipid in an organic solvent;
   ii) preparing a solution of coenzyme Q10 in an organic solvent;
   iii) mixing the solution obtained in step ii) with the suspension obtained in step i);
   iv) stirring the suspension obtained in step iii) at a temperature between 40° C. and 70° C.;
   v) removing the solvent from the suspension obtained in step iv).

2. A pharmaceutical or nutraceutical formulation for oral administration containing the solid dispersion according to claim 1 and a pharmaceutically or food acceptable excipient.

3. The solid dispersion according to claim 1 wherein the phospholipid is selected from the group consisting of lecithins from soy, sunflower or egg, phosphatidyl choline, phosphatidyl serine and phosphatidyl ethanolamine.

4. The solid dispersion according to claim 1 wherein the Coenzyme Q10 to cellulosic derivative ratio is 0.2 to 2.

5. The solid dispersion according to claim 4 wherein the Coenzyme Q10 to cellulosic derivative ratio is 0.5 to 1.

6. The solid dispersion according to claim 1 comprising Coenzyme Q10, a phospholipid and one or more a cellulosic derivative selected from microcrystalline cellulose, hydroxypropylmethyl cellulose, methylcellulose.

7. The solid dispersion according to claim 6 wherein the phospholipid is a lecithin from soy, sunflower or egg.

8. The solid dispersion according to claim 1 wherein the organic solvent is selected from the group consisting of ethanol, acetone and ethyl acetate.

9. The solid dispersion according to claim 8 wherein the organic solvent is ethyl acetate.

* * * * *